United States Patent [19]

Van Dell et al.

[11] Patent Number: 5,377,673

[45] Date of Patent: Jan. 3, 1995

[54] INTRAUTERINE MONITORING DEVICE

[76] Inventors: Peter Van Dell, 78 Morning Glory Dr., Easton, 06612; Dennis Buonafede, 55 Mulberry Ln., Huntington, both of Conn. 06484

[21] Appl. No.: 35,045

[22] Filed: Mar. 22, 1993

[51] Int. Cl.⁶ .............................. A61N 5/00
[52] U.S. Cl. .................. 128/633; 128/698
[58] Field of Search ............... 128/632, 633, 634, 642, 128/664, 665, 670, 698; 607/115, 116, 126–128, 138

[56] References Cited

U.S. PATENT DOCUMENTS

| 4,476,871 | 10/1984 | Hon | 128/642 |
| 4,658,825 | 4/1987 | Hochberg et al. | 128/642 X |
| 4,873,986 | 10/1989 | Wallace | 128/670 |
| 4,928,691 | 5/1990 | Nicolson et al. | 128/633 |
| 4,938,218 | 7/1990 | Goodman et al. | 128/633 |
| 5,025,787 | 6/1991 | Sutherland et al. | 128/642 |
| 5,099,842 | 3/1992 | Mannheimer et al. | 128/633 |
| 5,154,175 | 10/1992 | Gunther | 128/633 |
| 5,184,619 | 2/1993 | Austin | 128/698 X |

Primary Examiner—Lee S. Cohen
Assistant Examiner—Samuel Gilbert
Attorney, Agent, or Firm—CTC & Associates

[57] ABSTRACT

An improved fetal monitoring device which incorporates sensors which permit the monitoring of inutero fetal heart rate, oxygen saturation, blood chemistry and eliminates the collection of such information during maternal contractions.

5 Claims, 3 Drawing Sheets

INTRAUTERINE MONITORING DEVICE

BACKGROUND OF THE INVENTION

Fetal monitoring during labor and birth has become standard procedure in obstetric centers in the United States. Typically during early stages of labor extrauterine ultrasound probes placed on the maternal abdomen derive a signal which when processed yields fetal heart rate and maternal contractions. Subsequently, when labor has advanced to the point that the amniotic membranes have ruptured, the maternal cervix has dilated to 3 cm. and the fetus' head is presented, electrodes that penetrate the scalp are fastened to the fetus' displayed head. The signals picked up by this electrode are directed through multi-component processors yielding fetal heart rate (hereinafter FHR). Comparators in multi-component processors compare current FHR vs. FHR over time as well as a preprogrammed normal current FHR and FHR over time. Some systems have alarms incorporated into the circuits which are preset to alert the obstetric team (hereinafter OBT) that FHR is too high/too low, etc. The thus measured FHR is one of the means of detecting fetal distress. Based on FHR plus ultrasound viewing of the fetus and maternal medical indications the OBT may take other action such as inserting probes through cervical os to measure amniotic fluid pressure and maternal contraction pressure. In some cases, such as prolonged labor or early rupture of the membranes, synthetic amniotic fluid may be infused into the uterus to relieve fetal distress. In other instances the OBT may reach the conclusion that labor should be terminated by cesarian delivery.

In many cesarian deliveries triggered by FHR information it has been found that the fetus was not really in critical distress and could have been vaginally delivered in normal fashion.

One of the shortcomings of the state of the art systems is the variability of FHR which may change quite dramatically during maternal contractions. This information gathered by the sensors attached to the fetus' scalp is processed by multi-processors and is included in the readout of average FHR vs. actual and time line FHR. This processed information may lead the OBT to conclude there is fetal distress. However, this may not be the case, merely FHR slowing because of extracranial pressure caused by the maternal contractions.

Alternatively such processed FHR readings may not show actual fetal distress.

OBJECT OF THE INVENTION

The primary object of the invention is to supply the OBT with specific medical information about an inutero fetus during maternal labor to properly assess fetal well being.

An important object of the invention is to provide sensors which permit the monitoring of FHR, blood chemistry blood oxygen saturation and to eliminate the processing of FHR and blood chemistry information during maternal contraction cycles.

It is another important object of the invention to supply the OBT information regarding arterial blood flow to the scalp and by extrapolation to the brain.

PRIOR ART

The following art was found in a preliminary search for patentability.

U.S. Pat. No. 5,088,497—February, 1992—Ikeda—processing apparatus correlated between maternal pain intensity and fetal heart rate. Division of U.S. Pat. No. 5,069,218.

U.S. Pat. No. 5,046,965—September, 1991—Neese et al.—connector for coupling fetal scalp electrodes and maternal body for base references.

U.S. Pat. No. 5,042,499—August, 1991—Frank et al.—apparatus to non-invasively obtain from the maternal abdomen fetal ECG signal.

U.S. Pat. No. 5,025,787—June, 1991—Sutherland et al.—intrauterine probe which monitors Fetal Heart Rate and pressure sensor to develop intrauterine pressure.

U.S. Pat. No. 5,012,811—May, 1991—Malis—apparatus to affix fetal electrode to fetal scalp with OBT protective shield.

U.S. Pat. No. 4,951,680—August, 1991—Kirk et al.—apparatus to filter and process FHR signals from an electrode affixed to a fetus to establish changes or variation in the FR electrocardial interval which is useful to indicate fetal acidosis.

U.S. Pat. No. 4,945,917—August, 1990—Akselrod et al.—apparatus and method for displaying Fetal R-wave while eliminating maternal R-wave signal.

U.S. Pat. No. 4,934,371—June, 1990—Malis et al.—Spiral scalp electrode fetal monitoring device with protective shield to protect OBT.

U.S. Pat. No. 4,898,179—February, 1990—Sirota—Device for monitoring of fetal and maternal vital signs also permitting communication between mother and her fetus.

U.S. Pat. No. 4,890,624—January 1990—Ganguly et al.—Ultrasound doppler signal processor to determine FHR.

U.S. Pat. No. 4,873,986—October, 1989—Wallace—disposable uterus invasive apparatus for monitoring intrauterine pressure and FHR.

U.S. Pat. No. 4,781,200—November, 1988—Baker—Continuous ambulatory non-invasive fetal well being monitor apparatus.

U.S. Pat. No. 4,722,730—February, 1988—Levy et al.—uterine invasive apparatus for simultaneously monitoring intrauterine pressure and delivering infusible fluids for relief of fetal distress.

U.S. Pat. No. 4,644,956—February, 1987—Morgtenstern—fetal scalp electrode adapted to be transcervically fixed to the fetus.

None of the above combine the features of the instant invention nor method of affixing sensors to the fetus.

Other prior art which may be of interest follows.

U.S. Pat. No. 4,830,014—May, 1989—Goodman et al.—conformal sensor for transillumination of blood perfused portion of flesh to measure light extinction.

U.S. Pat. No. 4,700,708—October, 1987—New et al.—probe for use with an optimal oximeter.

U.S. Pat. No. 4,621,643—November, 1981—New et al.—solid state monitor for determination of oxygen saturation and pulse rate.

U.S. Pat. No. 4,167,331—September, 1979—Nielson—Multi-wavelength increment absorbance oximeter.

U.S. Pat. No. 3,998,550—December, 1976—Konishi et al.—photoelectric oximeter.

U.S. Pat. No. 3,847,483—November, 1972—Shaw et al.—optical oximeter apparatus and method.

U.S. Pat. No. 3,704,706—December, 1972—Herezfeld et al.—photo electric apparatus for detection of pulse rate and oxygen content of blood.

U.S. Pat. No. 3,638,640—February, 1972—Shaw—oximeter method and apparatus to determine oxygen saturation of blood.

U.S. Pat. No. 2,706,927—April, 1955—Wood—apparatus for determining percentage of oxygen saturation of blood.

SUMMARY OF THE INVENTION

In its simplest form the instant invention utilizes ongoing spectrophotomeric analysis of fetal blood in combination with or without pressure switches and pressure measuring devices which are combined in a single unit which is easily applied inutero to fetal flesh. Many other devices have been devised to measure individual parameters such as intrauterine pressure and fetal heart rate. None of the devices found in commerce or prior art reveal a device which monitors in utero fetal blood oxygen content, blood chemistry, maternal contraction pressure as well as eliminating information gathered during maternal contractions. The elimination of this information is important since the changes in FHR measured during maternal contractions may reflect normal physiological response but if averaged into ongoing FHR monitoring may distort the overall FHR information. The most common spectrophotometric analyzers in use are oximeters of the prior art. They function by transillumination of flesh with tuned wavelength light and a receiver or sensor tuned to be responsive to the absorption of wavelengths transmitted by the light source. The usual wavelength range of light source in these devices is in the near red range and specifically 540–580 nanometers range which is the range wherein absorption of light by single bound oxygen such as in hemoglobin is strongest. From such absorption data it is possible to determine total blood hemoglobin content and oxygen solution by determining the ratio of oxyhemoglobin to deoxyhemoglobin.

This information alone is a most useful monitoring tool to determine stress in an exutero patient because basic gravimetric or spectrogravimetric analysis of blood and urine have usually been or can be done to establish basic organ, cellular and metabolic function. This valuable base line information is not available nor readily obtainable in an inutero fetus.

It is one of the features of the invention to permit the instant ongoing non fetal invasive determination and ongoing monitoring of base line blood information. This is accomplished by use of transillumination of fetal flesh with an infrared light source and tuned receiver or sensor which is responsive to predetermined infrared absorption wavelengths. Most commonly indications of muscle damage, organ and cellular malfunction is by generation of chemicals in unusual amounts which become a constituent of blood. For example, measurable amounts of myoglobin indicates muscle damage. Similarly, significant amounts of aliphatic esters and ketones such as acetoacetone, acetone and b-hydroxybutyrate are indicative of cellular and organ malfunction.

Most of these chemicals exist as organic anions. The first indication of distress is an increase in total blood serum organic anion content (exclusive of protenate). Blood anion includes a great variety of individual ions of which lactate is usually most abundant to make up about 80% of the total organic anion fraction. The remaining 20% is made up of fatty acids, amino acids and others produced during normal metabolism. In various disease states some of these minor anions accumulate to significant concentrations. For example increase in total anion concentrates above 26 mmol/ion charges/l usually indicates renal problems. Similarly when lactate concentrations reach 25 mmol/l indicates lactic acidosis. Increase of keto acids, ketones and secondary alcohol acid ions may indicate metabolic problems and liver malfunction.

The organic aliphatic acids, amino acids, esters, ketone and alcohols have very narrow absorbancy characteristics in the infrared range wavelengths from 700–1,000 nanometer range. For example ionized aliphatic acid(anionic) absorb in the 700 nanometer range, aliphatic esters absorb in the 810 nanometer range and aliphatic ketones in the 840 nanometer range. Similarly double bound oxygen as found in myoglobin responds in the 825 nanometer range. Therefore the incorporation of CWLS and and tuned sensors that respectively radiate and sense absorption in the 540–590 and 700–825 nanometer range into a single device along with pressure switch and pressure measuring devices develops all of the data necessary for the OBT to assess ongoing fetal well being.

Perhaps the most significant early alerting of fetal distress is the detection of unusual amounts of organic anions (700 nanometers) which by extrapolation (i.e. every ionized anion must have a cation which is usually a Hydrogen ion) is an indication of possible low pH of fetal blood. Subsequent determination of the other components of the blood organic ion at other infrared wavelengths will provide the OBT with information as to the specific reason for the elevated organic ion level in the blood. This device can easily be adhered to a fetus' head or body via cervical insertion. The device is affixed to the fetus' head or body using well known transparent water based gel adhesives or alternatively affixed to the presented fetal scalp by the well known corkscrew FHR devices.

DETAILED DESCRIPTION

Figure 1:
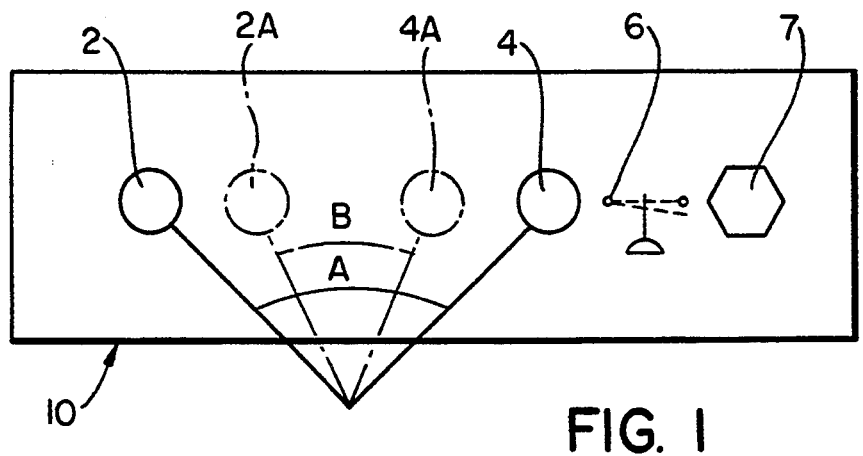
FIG. 1 is a plan view of the probe of the instant invention with CWLS tuned receiver, pressure switch and transducer.

FIG. 1 is a plan view of the sensor pad 10 of this invention which is designed to be intercervically adhered to the fetus' face or chest. It includes a controlled multi-wavelength light source (CWLS) such as a light emitting diode. A light sensor 4 which is responsive to the transilluminated wavelengths emitted by source 2, a pressure sensitive switch 6 and a pressure measuring device such as a transducer 7. Each of these devices have signal transmission cables (not shown) which are connected into microprocessors which are programmed to interpret absorption response to yield medical data such as pulse rate, blood chemistry and blood oxygen levels and intrauterally developed pressure. The placement of CWLS and receiver in proper relationship to each other is significant in supplying and sensing the reflected CWLS after passing through the cutaneous vascular area of the fetus. Experimentally it has been found that the angular relationship between the CWLS and sensors should at maximum be an arc A of 90° locations 2–4 and at minimum but no less than an arc B of 45° locations 2A–4A. Deviation from this range significantly changes the ability of the sensor to pick up proper absorption of radiated light to be transmitted to the interpreting microprocessor. The function of pressure switch 6 is to shut down transmission of sensor 4–4A when maternal contractions occur as when device 10 is applied intercervically to fetus' scalp, face, neck or body area FIG. 5 and adhered with an optically transparent gelatin adhesive 42 FIG. 4. In this location CWLS 2(2A) illuminates fetus' head cutaneous area and sensor 4(4A) generates signal which is transmitted to the microprocessor. Since pressure switch 6 stops transmission of that signal when contractions force fetal head into cervical area there is no need for circuitry or programming to interpret the signal as it changes in pulse rate, blood flow rate, blood oxygen level or blood chemistry. Thus only unstressed fetal non-maternal contracting pulse rate, blood flow rate, blood oxygen and chemistry are microprocessed eliminating the gathering of information which may cause the OBT to falsely determine that the fetus is distressed. Transducer 7 continues to function thus supplying OBT with maternal contracting pressure to assist in determining the progression of labor. The transducer 7 should have a sensitivity of range from 10 PSI (0.70 kg/sq.cm.) through 80 PSI (5.63 kg/sq.cm.) to function reasonably as a maternal contraction pressure indicator. This range of maternal contracting pressure is well known having previously been developed by intrauterine devices of the prior art.

Figure 4:
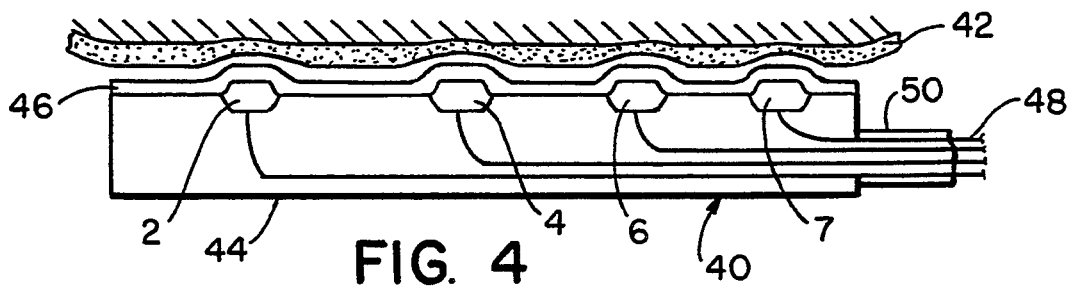
FIG. 4 is a side view of FIG. 1 illustrating layer of gel adhesive layer to affix to fetus.
Figure 5:
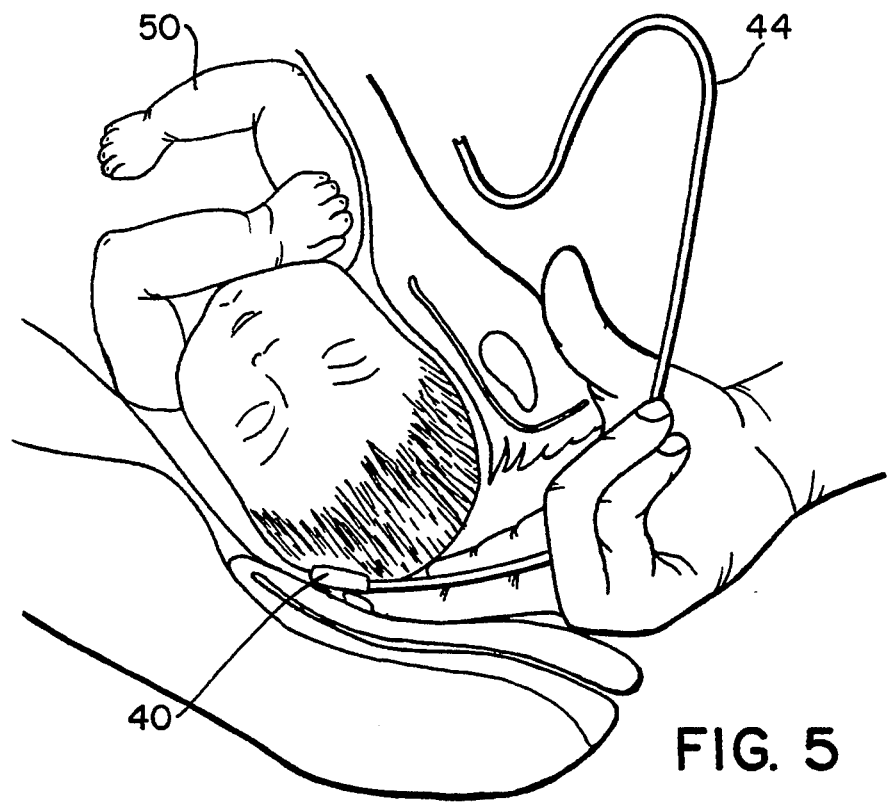
FIG. 5 is a sagittal view demonstrating placement of device on fetus' head.

The laminate sensor pad of the instant device 40 FIG. 4 is made up of three layers, the first of which is a transparent adhesive layer 42 the second a transparent film 46 which covers the CWLS, responsive sensor, pressure responsive switch and transducers and a bottom conforming layer 44. The CWLS responsive sensor, pressure responsive switch, transducer and interconnect wires 48 in cable 50 being sandwiched between the bottom layer and transparent film.

The gel adhesives utilized in bonding the pad to fetus are known and are largely commercially available. Such gels are colloids in which the disperse phase has been combined with the continuous phase. They are usually transparent. Flow, adhesive qualities and compatability with various body fluids are determined by formulation and rate of cooling a solution wherein the solutes form submicroscopic crystalline particle groups which retain solvents and other formulating chemicals in the interstices of the crystalline particles (so called brush heap structure). Specific formulations of these adhesives do not irritate even tender neonatal skin and are easily washed off the delivered infant.

Figure 2:
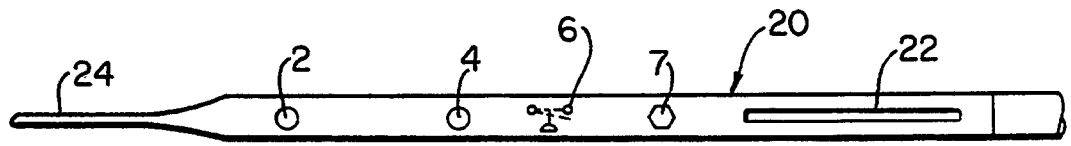
FIG. 2 is a plan view of an intrauterine lariat probe.
Figure 3:
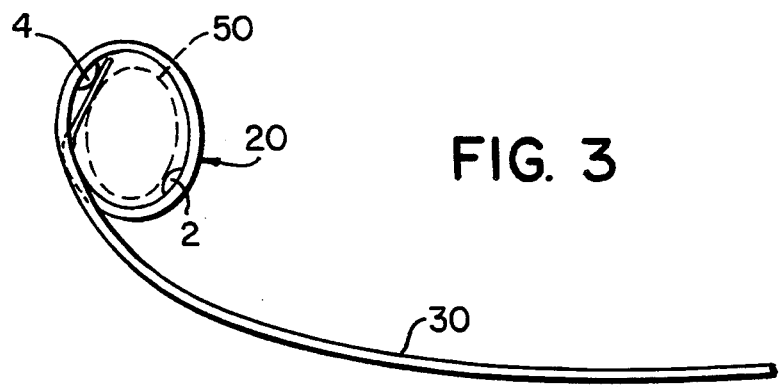
FIG. 3 is a side view of an intrauterine lariat probe affixed to fetus' extremity.
Figure 6:
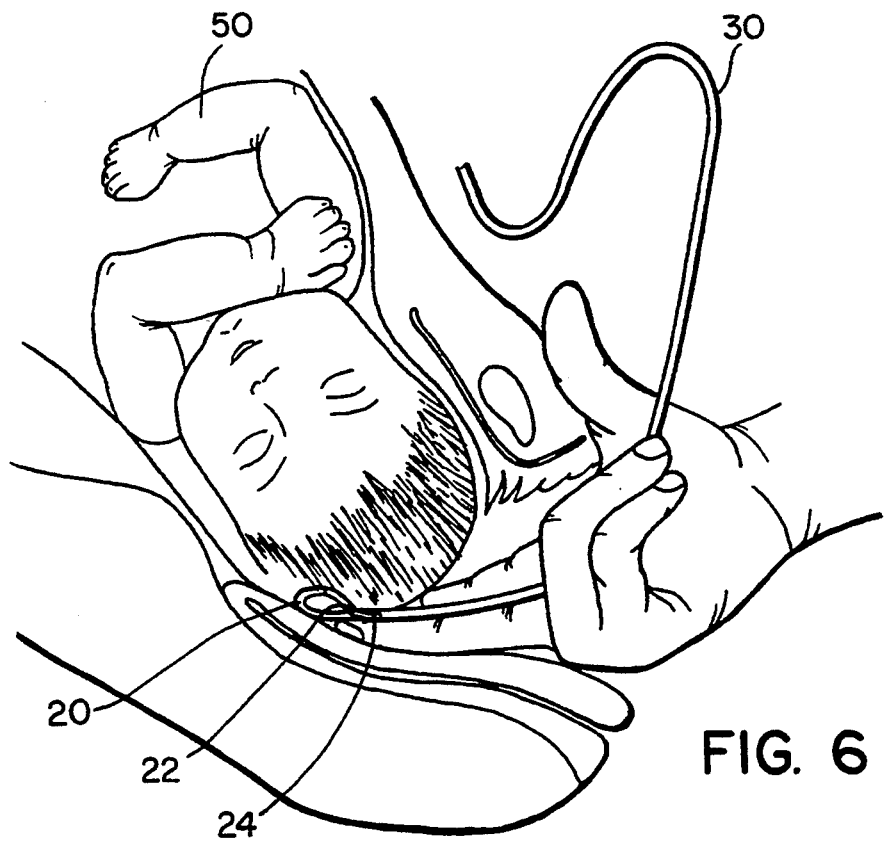
FIG. 6 is a sagittal view demonstrating proper initial insertion of lariat device.
Figure 7:
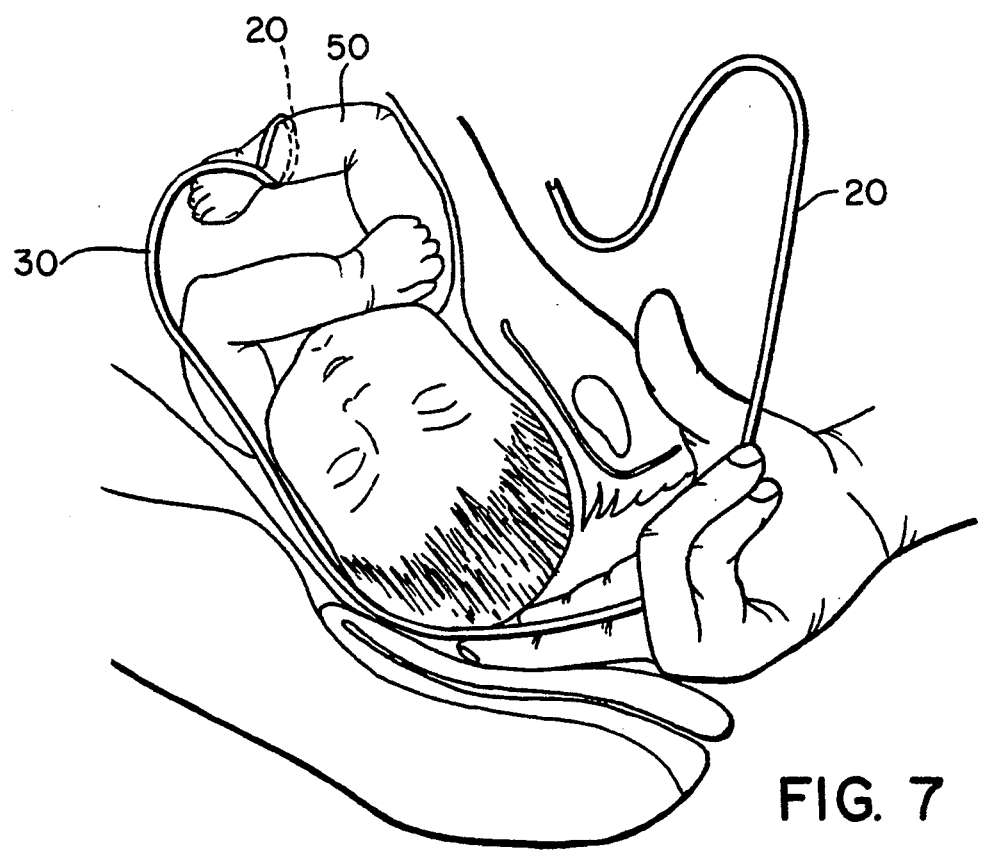
FIG. 7 is a sagittal view of proper ensnarement of fetal extremity.

FIG. 2, a second variation of the instant invention, is designed for intrauterine application wherein the components of sensor pad 10 are incorporated onto a lineal semi-flexible member 20 which may be plastic with controlled flexural modulus. End member 24 friction fits into slit 22 forming a lariat. The lariat FIG. 3 which is affixed to semi-flexible tube member 30 which also must have a controlled flexural modulus. The assembly of 20 and 30 when formed into a lariat is passed through the cervix by the OB after the membranes have ruptured FIG. 6. Thence by manipulation device 20 by tube 30, which is usually followed by ultrasound imaging, the OB snares fetus' extremity 50. Device 20 is then tightened to bring CWLS 2, tuned sensor 4, pressure switch 6 and transducer 7 in contact with fetus' extremity 50. Rapid release of formed lariat requires only a tug by the OB to have end 24 clear from friction fit slit 22. The device and connecting tube are then easily removed from the uterus via the dilated cervix.

Figure 8:
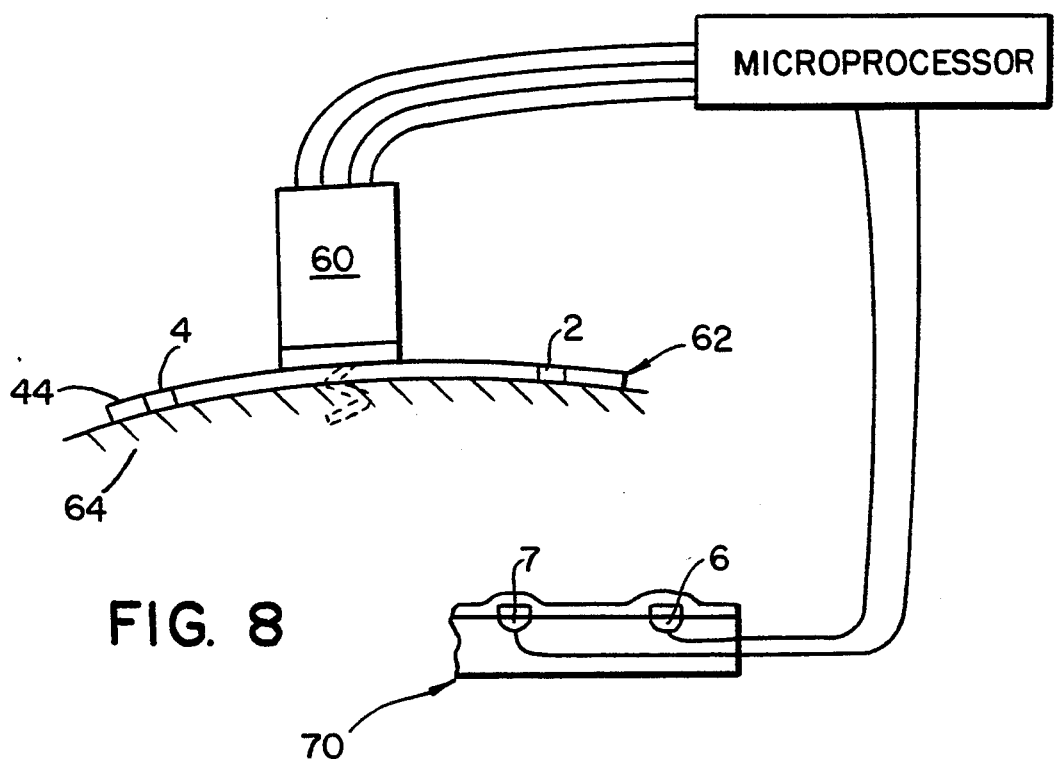
FIG. 8 is a side view of CWLS and tuned sensor, mounted on known corkscrew scalp electrode.

In another variation, the device 10 is affixed to the commonly used scalp electrode. In this instance the backing material 44 for pad 62 shown in FIG. 8 is made of a somewhat springing plastic which has been formed into a slight concave arc so that as scalp electrode is screwed into fetus' scalp 64 it contacts fetus' scalp with slight spring conforming to the radius of the fetus' head to ensure scalp contact of CWLS 2 and sensor 4. In this form the device does not include a pressure switch or pressure measuring means, only CWLS and controlled wavelength light sensor. The device as shown has a separate backing but it should be understood that the CWLS and light sensor could be incorporated directly into the base of a modified scalp electrode as long as the geometry of separation of CWLS and sensor is maintained. This compound device will permit the ongoing FHR as well as the other essential fetal medical information. In order to block out response during maternal contractions it is coupled with a separate device 70 FIG. 8 with pressure switch 6 and transducer 7 which monitors maternal contraction and pressure and blocks transmission of FHR and CWLS reflection during maternal contraction as aforesaid transmission of information from the sensor to the microprocessor is interrupted during maternal contractions thus eliminating information which may reflect on fetal distress during maternal contractions. A transparent gel may be used under the CWLS and sensor to eliminate extraneous information which may develop because of contamination of the fetal scalp. The composite device 62 can readily be removed in normal fashion just prior to fetus' head passing through the cervix.

The instant invention may incorporate a single CWLS and receiver to be responsive to absorption of such emitted radiation.

Alternatively, multiple individually tuned CWLS and multiple individually tuned sensors may be used particularly if they are tuned to respond to the desired wavelengths for optimum absorption for given blood components.

It is thought that the above described device will be most useful for inuterine fetus monitoring to be able to more clearly define fetal stress during delivery to better be able to determine if and when c-section delivery is required.

The present invention may be embodied in other specific forms without departing from its spirit or essential characteristics. As such, the scope of the invention is therefore indicated in the appended claims rather than by the foregoing description. All changes which come within the meaning and range of equivalency of the claims are to be embraced within their scope.

What we claim is:

1. An intrauterine fetal monitoring device to supply medical information including stages of maternal labor and degrees of fetal distress during delivery, the device comprising: a laminate sensor pad, said sensor pad having spatially located therein a controlled wavelength light source(CWLS) for transilluminating a fetus' cutaneous area, a sensor responsive to said CWLS and producing a first signal responding to said transillumination, a transducer for generating a second signal in response to intrauterine pressure during maternal contractions, and a switch means responsive to said second signal for interrupting the first signal during maternal contractions, and a microprocessor, said transducer and said sensor being connected to said microprocessor which delivers the medical information.

2. The device according to claim 1 wherein said pad has first, second, and third layers, said first layer being a transparent adhesive, said second layer being a transparent film and said third layer being a conforming layer, wherein said CWLS sensor, switch means, and transducer along with interconnecting wires are linearly arranged into said pad between said second and third layers.

3. The device according to claim 2 wherein said transparent adhesive is a tacky gelatinous mass which is non-fetal irritating, amniotic fluid compatible and removable with water.

4. A fetal monitoring device for supplying medical information on stages of maternal labor and degrees of fetal distress during delivery, the device comprising a releasable lariat formed from controlled flexural modulus lineal members, said lariat having an inner surface, said device further comprising a controlled wavelength light source(CWLS) for transilluminating a fetus' cutaneous area, a sensor responsive to said CWLS for producing a first signal, a transducer for generating a second signal in response to intrauterine pressure during maternal contractions, and a switch means responsive to said second signal for interrupting the first signal during maternal contractions, said light source, sensor, transducer, and switch means affixed to said inner surface, a microprocessor, said transducer and said sensor being connected to said microprocessor which delivers the medical information, further, said lariat including means for ensnaring a fetus' extremity to bring the CWLS, sensor, and transducer in contact with the fetus' extremity.

5. A fetal monitoring device for supplying medical information on fetal blood chemistry and stages of labor, the device comprising a scalp monitor coupled with an intrauterine probe, said monitor having a controlled wavelength light source(CWLS) for transilluminating a fetus' cutaneous area, a sensor responsive to said CWLS for producing a first signal, a transducer for generating a second signal in response to intrauterine pressure during maternal contractions, and a switch means responsive to said second signal for interrupting the first signal during maternal contractions, further, said monitor including means for mounting on a fetus' scalp to bring the CWLS, sensor, and transducer in contact with the scalp.

* * * * *